United States Patent [19]
Thomas et al.

[11] Patent Number: 6,037,497
[45] Date of Patent: Mar. 14, 2000

[54] PROCESS FOR PRODUCING AMINE OXIDES

[75] Inventors: Dustin H. Thomas, Baton Rouge, La.; Douglas H. Krzystowczyk, Orangeburg, S.C.; Luc G. Six, Wijnegem, Belgium

[73] Assignee: Albemarle Corporation, Richmond, Va.

[21] Appl. No.: 09/162,956

[22] Filed: Sep. 29, 1998

[51] Int. Cl.⁷ .................................................. C07C 292/02
[52] U.S. Cl. ............................................ 564/298; 564/301
[58] Field of Search ................................... 564/301, 298; 561/301

[56] References Cited

U.S. PATENT DOCUMENTS

| | | | |
|---|---|---|---|
| 3,332,999 | 7/1967 | Mitchell et al. | 260/583 |
| 4,247,480 | 1/1981 | Murata | 564/298 |
| 4,748,275 | 5/1988 | Smith et al. | 564/298 |
| 4,942,260 | 7/1990 | Laurenzo | 564/298 |
| 4,960,934 | 10/1990 | Smith et al. | 564/298 |
| 4,970,340 | 11/1990 | Smith | 564/298 |
| 4,994,614 | 2/1991 | Bauer | 564/300 |
| 5,075,501 | 12/1991 | Borland et al. | 564/297 |
| 5,082,940 | 1/1992 | Legrand et al. | 544/353 |
| 5,130,488 | 7/1992 | Smith | 564/298 |
| 5,208,374 | 5/1993 | Borland | 564/298 |
| 5,223,644 | 6/1993 | Blezard | 564/2 |
| 5,254,735 | 10/1993 | Smith | 564/298 |
| 5,292,954 | 3/1994 | Borland et al. | 564/298 |
| 5,442,113 | 8/1995 | Blezard et al. | 564/2 |
| 5,498,373 | 3/1996 | Miller et al. | 252/546 |
| 5,498,791 | 3/1996 | Blezard et al. | 564/2 |
| 5,693,861 | 12/1997 | Smith | 564/298 |
| 5,710,333 | 1/1998 | Bader | 564/298 |

FOREIGN PATENT DOCUMENTS 307184  3/1989  European Pat. Off. .

OTHER PUBLICATIONS

WPIDS Abstract of JP 51032505, dated Mar. 19, 1976.
CAPLUS Abstract of JP 51032505, dated Mar. 19, 1976.

*Primary Examiner*—Paul J. Killos
*Assistant Examiner*—Jean F. Vollano
*Attorney, Agent, or Firm*—E. E. Spielman, Jr.

[57] ABSTRACT

A process is described in which tertiary amine is oxidized with hydrogen peroxide in the presence of carbon dioxide until the reaction mass contains (i) about 0.5 to about 6.5%, and preferably about 1 to about 2.5%, of unreacted free amine, (ii) carbon dioxide, and (iii) unreacted hydrogen peroxide. At this point individual portions of the reaction mass are dispensed into a plurality of shipping containers, or alternatively, the reaction mass is transferred to a cooling vessel, cooled therein, and then dispensed into a plurality of shipping containers. Thereafter the reaction is allowed to slowly continue to completion at ambient temperature in the shipping containers with venting of off-gases, as required. The process makes it possible to produce amine oxides with increased plant throughput without need for additional plant reaction equipment such as glass-lined reactors, and the consequent substantial additional capital investment. Also the process enables production of amine oxides having, if any, very low levels of nitrosoamine impurities without increasing reactor residence time and without need for such additional plant reaction equipment and associated additional capital outlay.

25 Claims, No Drawings

PROCESS FOR PRODUCING AMINE OXIDES

U.S. Pat. No. 4,247,480 describes an efficacious process for producing amine oxides. Despite the improvements in reaction rate achieved in the process of that patent, it would be of great advantage if a way could be found to make it possible to produce amine oxides with increased plant throughput without need for additional plant reaction equipment such as glass-lined reactors, and the consequent substantial additional capital investment. It would also be of great advantage if a way could be found to enable production of amine oxides having, if any, very low levels of nitrosoamine impurities (a.k.a. nitrosamine, and which are suspected carcinogenic impurities) without increasing reactor residence time and without need for such additional plant reaction equipment and associated additional capital outlay.

This invention makes all of this possible by providing a novel process for the production of amine oxides.

In one of its embodiments this invention provides a process which comprises:
 a) oxidizing tertiary amine with hydrogen peroxide in the presence of carbon dioxide until the reaction mass contains (i) unreacted free amine in the range of about 0.5 to about 6.5%, and preferably in the range of about 1 to about 2.5%, of the reaction mass, (ii) carbon dioxide, and (iii) unreacted hydrogen peroxide;
 b) dispensing individual portions of the reaction mass into a plurality of shipping containers, or alternatively, transferring at least a portion of the reaction mass to a cooling vessel, allowing or causing the reaction mass in said vessel to cool therein, and then dispensing individual portions of the cooled reaction mass into a plurality of shipping containers; and
 c) thereafter allowing the reaction to slowly continue to completion at ambient temperature in a plurality of such shipping containers with venting of off-gases, as required.

The amount of unreacted hydrogen peroxide relative to the amount of unreacted free amine remaining in step a) above should be sufficient to convert enough of the free amine into amine oxide such that the manufacturer's specifications on amine oxide and free amine contents are complied by virtue of the slow continued reaction that takes place in step c) above. Usually the amount of unreacted hydrogen peroxide remaining in step a) will be sufficient to convert at least about 50% of the unreacted free amine into amine oxide. Preferably there will be approximately a stoichiometric amount or a slight excess of unreacted hydrogen peroxide remaining in step a) relative to the amount of unreacted free amine remaining in step a).

In a preferred embodiment tertiary amine oxide is produced by a process which comprises:
 a) oxidizing tertiary amine with hydrogen peroxide in the presence of carbon dioxide at a temperature in the range of about 50 to about 60° C. until the reaction mass contains (i) unreacted free amines in the range of about 0.5 to about 6.5%, and preferably in the range of about 1 to about 2.5%, of the reaction mass, (ii) carbon dioxide, and (iii) unreacted hydrogen peroxide;
 b) dispensing individual portions of the reaction mass at a temperature in the range of about 35 to about 60° C. into a plurality of shipping containers; and
 c) thereafter allowing the reaction to slowly continue to completion at ambient temperature in a plurality of such shipping containers with venting of off-gases, as required.

Typically and preferably, step a) of the process of this invention is conducted in a reactor having suitably inert interior surfaces, preferably a glass-lined reactor, and the shipping containers, such as shipping drums, also have suitably inert interior surfaces. By suitably inert interior surfaces is meant that the interior surfaces that contact or may come in contact with the reaction mass do not contain appreciable amounts of iron, nickel, magnesium, manganese or any other metal or metalloid that can form detrimental metallic or metalloid impurities in the reaction mass or amine oxide product that come in contact with such surface, or that could act to decompose residual hydrogen peroxide required to convert the unreacted tertiary amine into the tertiary amine oxide product once the material has been transferred to the shipping containers. Thus, the suitably inert surface is preferably composed of glass, or a suitable polymeric material, such as polyethylene, polypropylene, fiberglass-reinforced plastic (FRP), polytetrafluoroethylene (PTFE), polyvinylidene difluoride (PVDF), or any other appropriate equivalent material. For example, the reactor in which the principal initial oxidation reaction is performed, and if used, any intermediate cooling vessel for the reaction mass, preferably has a glass lining, although it is possible to use a reactor or vessel composed of or lined with a suitably-passivated stainless steel alloy. The shipping containers are preferably polyethylene shipping drums, or liquid tote bins made of polyethylene. The shipping containers are preferably equipped with microporous vent plugs which serve to vent off-gases from the final stages of the oxidation reaction occurring in the container. An example is Florida Drum No. EZH-2 equipped with 2-inch HPBMP-VO microporous vent plug, or equivalent container or vent plug. While use of reactors and containers having such suitably inert interior surfaces is not essential, the use thereof results in the formation of aqueous tertiary amine oxide products of substantially greater purity.

Aliphatic tertiary amines such as referred to in U.S. Pat. No. 4,247,480 can be used in the process of this invention. For example, the tertiary amine used in forming the tertiary amine oxide can have the formula

wherein $R_1$ and $R_2$ are, independently, methyl or ethyl groups and $R_3$ is an aliphatic, monovalent hydrocarbon group containing in the range of 8 to 14 carbon atoms. Typically, the hydrocarbyl groups are alkyl groups, or are alkenyl groups each of which contains one or two olefinic double bonds. $C_{12}$ and $C_{14}$ straight chain alkyl groups are preferred. Exemplary of suitable tertiary amines are decyldimethyl amine, undecyldimethyl amine, dodecyldimethyl amine, tetradecyldiethyl amine, dodecylethylmethyl amine, tridecyldimethyl amine, tetradecyldimethyl amine, dodecyldiethyl amine, tetradecylethylmethyl amine, lauryldimethyl amine, myristyldimethyl amine, lauryldiethyl amine, laurylethylmethyl amine, myristylethylmethyl amine, myristyldiethyl amine, and the like. Preferred are dodecyldimethyl amine and tetradecyldimethyl amine.

The hydrogen peroxide is best employed as an aqueous solution. While hydrogen peroxide solutions can have a concentration of 5 to 70 wt % of hydrogen peroxide, preferred solutions contain 30 to 70 wt % of hydrogen peroxide.

Typically, the proportions of hydrogen peroxide to tertiary amine used in step a) will fall in the range of about 1 to about 1.1, and preferably in the range of about 1.02 to about 1.06, moles of hydrogen peroxide per mole of tertiary amine. When conducting step a) of the process of this invention, it is possible to choose to provide for a sufficient excess of hydrogen peroxide at the beginning of the reaction of step a) to obtain a 0.15 to 1.0 wt % hydrogen peroxide concentration in the final amine oxide product which gives viscosity and color benefits to the amine oxide product.

The reaction mixture formed in step a) can, and preferably does, contain at least one suitable chelating agent such as ethylenediamine tetraacetic acid or a water-soluble salt thereof, diethylene-triamine pentaacetic acid or a water-soluble salt thereof, or S,S-ethylenediamine disuccinic acid or a water-soluble salt thereof. Other suitable chelating agents include nitrilotriacetic acid or a water-soluble salt thereof. The chelating agent, which serves as a sequestrant for metal ions which may be derived by extraction from metallic reactor walls, piping or the like, is preferably a metal-free chelating agent. In this way the chelating agent as added to the reaction mixture does not itself introduce any metal constituent(s). Thus, if used as a salt, it is preferably an ammonium salt, although because of the small amounts of chelating agent used, alkali metal salts such as the sodium salts are acceptable for use. Typically, the amount of chelating agent used will fall in the range of about 0.01 to about 0.1 wt %, and preferably in the range of about 0.05 to about 0.1 wt %, based on the total weight of the reaction mixture.

Of the chelating agents suitable for use, ethylenediamine tetraacetic acid, diethylenetriamine pentaacetic acid, and S,S-ethylenediamine disuccinic acid are the three most preferred materials.

Step a) is typically performed in an aqueous medium. Suitably pure water must be used in order to prevent appreciable decomposition of the peroxide. This in turn ensures that sufficient residual peroxide remains in the product mixture dispensed into the shipping containers to enable the continuing oxidation reaction to go to completion or at least to substantial completion so that the finished product will comply with the manufacturer's specification on maximum free amine content. The actual value for the free amine specification is, of course, dictated by market, economic, competitive, and technological considerations. A feature of this invention is that the maximum amount of free amine can be kept below 0.2 wt % without difficulty provided the water (and other reactants) are of suitable purity. Thus, the water used in step a) should be free of appreciable quantities of dissolved metals and other undesirable impurities. While it is not necessary to employ deionized or distilled water, such materials can be used if desired. Ordinary sources of water such as tap water can prove satisfactory provided the water is free of sediment and has a suitably high electrical resistivity, e.g., at least about $10^5$ ohm centimeters, and preferably at least about $10^6$ ohm centimeters. In general, the higher the resistivity, the better. Ordinarily, at least a portion of the water employed in producing the reaction medium will be provided by the aqueous hydrogen peroxide solution. However, oftentimes it is desirable to increase the amount of water over and above that provided by the aqueous hydrogen peroxide being used in making up the reaction mixture. In general, the amount of water should correspond in quantity to the quantity desired in the finished amine oxide solution to be produced in the process, as this eliminates the need for subsequent operations such as further dilution with water, or distillation of excessive quantities of water from the aqueous product solution produced in the reaction. Thus, if a 30 wt % solution of amine oxide is the target product, the total amount of water introduced into the reaction mixture should correspond to approximately 70 wt % of the projected total weight of the amine oxide solution being formed. Tertiary amine oxide solutions containing in the range of about 10 to about 50 wt % of the tertiary amine oxide can be readily produced by the practice of this invention, provided of course that the tertiary amine oxide has the requisite water solubility at ambient room temperature and, preferably, remains in solution at temperatures as low as about 5° C.

An essential ingredient charged to the reaction mixture is carbon dioxide. Although it may be charged in the form of so-called dry ice, it is preferable to introduce the carbon dioxide in gaseous form and to introduce the same at a locus below the surface of the liquid reaction mixture. The carbon dioxide serves as a reaction catalyst or reaction promoter. In this connection, the precise chemical make-up of the carbon dioxide-derived catalyst is not known with certainty. It may be that the carbon dioxide itself catalyzes or promotes the reaction. However, it is equally possible that the carbon dioxide reacts in situ to form either carbonic acid or some unidentified complex or other substance which serves as the actual catalytic entity. It will thus be understood that this invention is not limited to the particular form or chemical composition of the reaction catalyst or reaction promoter resulting from the introduction into the reaction mixture of carbon dioxide as an ingredient.

Typically, the amount of carbon dioxide introduced into the aqueous reaction mixture should be in the range of about 0.01 to about 0.5 wt %, and preferably in the range of about 0.05 to about 0.25 wt %, of the weight of the tertiary amine being used in step a).

The various ingredients making up the reaction mixture in step a) can be introduced into the reactor in a number of sequences. For example, each of the ingredients (tertiary amine, aqueous hydrogen peroxide, carbon dioxide, additional water if used, and chelating agent if used) can be introduced individually or in any suitable subcombinations and in any suitable order into the reactor in the total quantities to be used with no further feed of any ingredient during the course of the reaction. When conducting the reaction in this manner (i.e., with all of the ingredients charged at the outset), the only preference is that either the carbon dioxide or the aqueous hydrogen peroxide should be the last ingredient introduced into the reaction mixture, as the reaction will be initiated upon the introduction of either such ingredient to the mixture comprising the other such ingredient and the tertiary amine. Thus, in one such embodiment the aqueous reaction medium is formed by mixing together tertiary amine, carbon dioxide, optionally chelating agent, and optionally water, and then introducing aqueous hydrogen peroxide into the reaction mixture to initiate the exothermic reaction. In another such embodiment the aqueous reaction medium is formed by mixing together tertiary amine, aqueous hydrogen peroxide, and optionally chelating agent and/or additional water, and then introducing carbon dioxide to initiate the exothermic reaction. Still another such embodiment involves forming the reaction mixture by introducing tertiary amine, and optionally chelating agent and/or water, into a reactor, and then introducing concurrently or in any sequence, aqueous hydrogen peroxide and be the dioxide to initiate the exothermic reaction. In theory, the tertiary amine could be the last ingredient charged to the reaction mixture, however, this is less desirable as it could result in excessive premature oxidation of the tertiary amine with adverse consequences.

U.S. Pat. No. 4,247,480 specifies that the amine oxidation reaction is conducted at temperatures in the range of about 40 to about 80° C. However, significant amounts of nitrosoamines can be produced if the reaction is allowed run to completion or to near completion at the high temperatures exemplified in U.S. Pat. No. 4,247,480. Thus, while step a) of the process of this invention can be performed at temperatures in the range of about 40–80° C., it is distinctly preferably to conduct the oxidation of step a) at one or more temperatures in the range of about 50 to about 55° C. (i.e., to perform substantially all of the step a) reaction at a single selected temperature in this range or by causing or allowing the reaction temperature to vary or fluctuate within this range during substantially all of step a)). In this way the amount, if any, of nitrosoamines impurities in the product is significantly reduced.

At the conclusion of step a) the reaction mass should contain in addition to the tertiary amine oxide formed in the reaction, a suitable proportion of unreacted tertiary amine, a suitable amount, and most preferably a stoichiometric amount, of unreacted hydrogen peroxide relative to the amount of the unreacted tertiary amine remaining in the reaction mass, and carbon dioxide.

After conducting step a), two basic alternatives exist as step b). In one such alternative individual portions of the reaction mass are dispensed into a plurality of suitable shipping containers, and such dispensed portions of the reaction mass are either allowed to cool to a moderate temperature (e.g., in the range of about 35° C. to about room temperature) by letting the containers stand at room temperature for a suitable period of time) or are caused to cool to a suitable temperature such as in the range of about 10 to about 35° C., for example by placing the containers in a cold storage room for a suitable period of time. In the second alternative, at least a portion of the reaction mass is allowed or caused to cool to a suitable temperature (e.g., in the range of about 10 to about 35° C.), in the reactor or when desiring to increase reactor throughput, in a separate large cooling vessel, and then individual portions of the cooled reaction mass are dispensed into a plurality of shipping containers. The large cooling vessel, if used, can simply hold the reaction mass until the average temperature of the contents reaches about 10 to about 35° C. before dispensing to the individual shipping containers, or this vessel can be equipped with internal and/or external cooling means such as cooling coils through which a suitable cooling liquid is passed in order to effect heat exchange from the reaction mass to the coolant. Irrespective of whichever of these alternatives is used, the next step —step c)—involves allowing the reaction to slowly continue to completion at ambient temperatures in a plurality of such shipping containers with venting of off gases, as required.

The process of this invention makes possible the production of 30 wt % aqueous tertiary amine oxide products containing less than current specification limits of 100 ppb total nitrosoamines as NNO and less than 15 ppb as the volatile nitrosodimethylamines. Typical analyses are below detection limits of 15 and five ppb respectively. Current commercial products from other sources typically make product containing levels 10–100 times higher at best. In this connection, as used herein "ppb" means parts per billion parts, a billion being $10^9$ or a thousand million.

The following example of the process of this invention is presented for purposes of illustration and not limitation.

EXAMPLE

A 1500-gallon, glass-lined reactor equipped with a two-speed agitator of 40 and 80 RPM was rinsed with softened water, then passivated with a 30% nitric acid solution. Following the passivation, the reactor was rinsed with fresh water five additional times. During the final rinse, the pH of the reactor water was 7.7. The reactor was charged with 951 kg of tetradecyldimethyl amine (Albemarle Corporation), 1,931 kg of water, and 1 kg of diethylenetriamine pentaacetic acid chelator. The water used was provided from a water softening system, so that chloride was present in the water, and the pH of the water was 7.7. A test by FTR revealed the water to have a resistivity of 1.95 MΩ. To the reactor was also charged 1.3 kg of carbon dioxide via 0.5-inch SS tubing extending into the liquid reaction mixture. Then the feed of a total of 399 kg of 35% hydrogen peroxide was initiated. The hydrogen peroxide was gravity fed with the flow rate manually controlled by two ball valves, using the change in tank level for measuring the peroxide feed rate. The average $H_2O_2$ feed rate was 127.3 kgs/hr. During the hydrogen peroxide addition, the reactor contents were agitated at 80 RPM to maximize heat transfer, and the reaction temperature was maintained predominately at 50–55° C. with the maximum temperature being 57.5° C. Cooling water typically at 12° C. in a closed loop was used as needed to control the temperature. After the peroxide addition, the reactor contents were agitated at 40 RPM to minimize shear-induced foaming, and the temperature was not allowed to exceed about 55° C. An additional 2 kg charge of carbon dioxide was added to the reaction mixture after completion of the peroxide feed to assist in accelerating the reaction. During the reaction, the reactor was vented to the atmosphere, except during the addition of the carbon dioxide. After this final charge of carbon dioxide, the agitator was set at 40 RPM, and allowed to agitate for three hours. Then, the agitator was shut off, and the vent opened for the night. The next morning (17 hours from the start of the reaction) the agitator was turned on low (40 RPM), and the reactor was sampled. The aqueous reaction mass was found by analysis to contain 0.46 wt % unreacted tetradecyldimethyl amine, 0.37 wt % unreacted hydrogen peroxide and 30.7 wt % tetradecyldimethyl amine oxide. Analyses of the product mixture sampled 3.67 hours later, and 17 hours later showed the following:

| Time, hrs. | Peroxide, wt % | Free amine, wt % | Tertiary amine oxide, wt % |
|---|---|---|---|
| 3.67 | 1.40 | 4.40 | 29.0 |
| 17 | 0.37 | 0.46 | 30.7 |

After adjusting the water content by addition of 102 kg of water, the reaction mixture was dispensed at 40° C. into 55 gallon polyethylene drums equipped with vented bung plugs to vent any off-gases produced as the reaction continued. The product after standing in the drums for 6 weeks was sampled and found by analysis to contain 0.19 wt % unreacted tetradecyldimethyl amine, 0.08 wt % unreacted hydrogen peroxide, and 30.6 wt % tetradecyldimethyl amine oxide.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus, the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises," "is,", etc.), the reference is to the substance, component or ingredient as it existed at the time just before it was first contacted, blended or mixed with one or more other substances, components and/or ingredients in accordance with the present disclosure. The fact that the substance, component or ingredient may have lost its original identity through a chemical reaction or transformation during the course of such contacting, blending or mixing operations is thus wholly immaterial for an accurate understanding and appreciation of this disclosure and the claims thereof.

Likewise, the process of this invention produces "tertiary amine oxide" in an aqueous medium. By this is meant that if the water is removed one will recover tertiary amine oxide as a chemical product. While the "tertiary amine oxide" is in solution it may possibly be solvated, hydrated, complexed, or otherwise altered in chemical makeup, and if such actually happens, the claims hereinafter are intended to cover any such natural consequence of carrying out the process of this invention in the proper manner as described herein. Thus, it matters not if any such solvation, hydration, or other alteration in chemical makeup of the "tertiary amine oxide" occurs while in the aqueous medium as long as the process is being carried out properly as described and claimed herein. In short, the product of the process is identified as chemists identify products, and not as lawyers or others might seek to identify them.

Each and every patent or other publication referred to in any portion of this specification is incorporated in toto into this disclosure by reference, as if fully set forth herein.

This invention is susceptible to considerable variation in its practice. Therefore, the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process of producing a tertiary amine oxide, which process comprises:
    a) oxidizing tertiary amine with hydrogen peroxide in water in the presence of carbon dioxide and at a temperature in the range of about 50 to about 60° C. until the reaction mass contains (i) unreacted free amine in the range of about 0.5 to about 6.5% of the reaction mass, (ii) carbon dioxide, and (iii) unreacted hydrogen peroxide;
    b) dispensing individual portions of the reaction mass into a plurality of shipping containers, or alternatively, transferring at least a portion of the reaction mass to a cooling vessel, allowing or causing the reaction mass in said vessel to cool therein, and then dispensing individual portions of the cooled reaction mass into a plurality of shipping containers; and
    c) thereafter allowing the reaction to slowly continue to completion at ambient temperature in a plurality of such shipping containers with venting of off-gases, as required;
such that the product contains less than 100 ppb of total nitrosoamines as NNO and less than 15 ppb as volatile nitrosodimethylamines.

2. A process of claim 1 wherein a) is conducted in a reactor having suitably inert interior surfaces, and wherein said shipping containers comprise a plurality of shipping containers having suitably inert interior surfaces.

3. A process of claim 1 wherein b) is performed by dispensing individual portions of the reaction mass from said reactor into a plurality of shipping containers.

4. A process of claim 3 wherein a) is conducted in a reactor having suitably inert interior surfaces, and wherein said shipping containers comprise a plurality of shipping containers having suitably inert interior surfaces.

5. A process of claim 1 wherein b) is performed by dispensing at least a portion of the reaction mass from said reactor into a separate cooling vessel, allowing or causing the reaction mass in the cooling vessel to cool therein, and then dispensing individual portions of the cooled reaction mass from said vessel into a plurality of said shipping containers.

6. A process of claim 5 wherein a) is conducted in a reactor having suitably inert interior surfaces, wherein said cooling vessel has suitably inert interior surfaces, and wherein said shipping containers comprise a plurality of shipping containers having suitably inert interior surfaces.

7. A process of claim 1 wherein the reaction mass dispensed in b) contains in the range of about 1 to about 2.5% of unreacted free amine and sufficient unreacted hydrogen peroxide to convert at least 50% of such unreacted free amine to amine oxide.

8. A process of claim 1 wherein the reaction mass dispensed in b) contains in the range of about 1 to about 2.5% of unreacted free amine and at least an equimolar amount of unreacted hydrogen peroxide relative to such unreacted free amine.

9. A process of claim 1 wherein said tertiary amine has two methyl or ethyl groups and an alkyl group having in the range of about 6 to about 14 carbon atoms or an alkenyl group having in the range of about 6 to about 14 carbon atoms and from 1 to 2 olefinic double bonds.

10. A process of claim 1 wherein said tertiary amine is dodecyldimethyl amine or tetradecyldimethyl amine.

11. A process of producing a tertiary amine oxide, which process comprises:
    a) oxidizing tertiary amine with hydrogen peroxide in water in the presence of carbon dioxide while maintaining the reaction mass at a temperature in the range of about 50 to about 60° C. until the reaction mass contains unreacted free amines in the range of about 0.5 to about 6.5% of the reaction mass, which also contains unreacted hydrogen peroxide and carbon dioxide;
    b) dispensing individual portions of the reaction mass at a temperature in the range of about 35 to 60° C. into a plurality of shipping containers; and
    c) thereafter allowing the reaction to slowly continue to completion at ambient temperature in a plurality of such shipping containers with venting of off-gases, as required;
such that the product contains less than 100 ppb of total nitrosoamines as NNO and less than 15 ppb as volatile nitrosodimethylamines.

12. A process of claim 11 wherein a) is conducted in a reactor having suitably inert interior surfaces, and wherein said shipping containers comprise a plurality of shipping containers having suitably inert interior surfaces.

13. A process of claim 12 wherein a) is conducted in a glass-lined reactor, and wherein said shipping containers comprise a plurality of shipping drums having suitably inert interior surfaces and microporous vent plugs.

14. A process of claim 11 wherein in a) the tertiary amine is oxidized with hydrogen peroxide in the presence of carbon dioxide until the reaction mass contains in the range of about 1 to about 2.5% of the original tertiary amine reactant fed and the reaction mass also contains at least a stoichiometric amount of unreacted hydrogen peroxide relative to the amount of the tertiary amine remaining in the reaction mass, and carbon dioxide.

15. A process of claim 11 wherein said tertiary amine has two methyl or ethyl groups and an alkyl group having in the range of about 6 to about 14 carbon atoms or an alkenyl group having in the range of about 6 to about 14 carbon atoms and from 1 to 2 olefinic double bonds.

16. A process of claim 11 wherein said tertiary amine is dodecyldimethyl amine.

17. A process of claim 11 wherein said tertiary amine is tetradecyldimethyl amine.

18. A process of claim 14 wherein said tertiary amine has two methyl or ethyl groups and an alkyl group having in the range of about 6 to about 14 carbon atoms or an alkenyl group having in the range of about 6 to about 14 carbon atoms and from 1 to 2 olefinic double bonds, wherein a) is conducted in a reactor having suitably inert interior surfaces, and wherein said shipping containers comprise a plurality of shipping containers having suitably inert interior surfaces.

19. A process of claim 18 wherein said tertiary amine is dodecyldimethyl amine or tetradecyldimethyl amine, wherein a) is conducted in a glass-lined reactor, and wherein said plurality of shipping drums have microporous vent plugs.

20. A process of claim 1 wherein the oxidation of step a) is conducted at one or more temperatures in the range of about 50 to about 55° C. during substantially all of step a), wherein a chelating agent is included in the reaction mixture of step a) in an amount in the range of about 0.01 to about 0.1 wt % based on the total weight of the reaction mixture, and wherein about 1 to about 1.1 moles of hydrogen peroxide per mole of tertiary amine are employed in forming the reaction mixture of step a).

21. A process of claim 11 wherein the oxidation of step a) is conducted at one or more temperatures in the range of about 50 to about 55° C. during substantially all of step a).

22. A process of claim 21 wherein said tertiary amine has two methyl or ethyl groups and an alkyl group having in the range of about 6 to about 14 carbon atoms or an alkenyl group having in the range of about 6 to about 14 carbon atoms and from 1 to 2 olefinic double bonds, wherein step a) is conducted in a reactor having suitably inert interior surfaces, and wherein said shipping containers comprise a plurality of shipping containers having suitably inert interior surfaces.

23. A process of claim 22 wherein a chelating agent is included in the reaction mixture of step a) in an amount in the range of about 0.05 to about 0.1 wt % based on the total weight of the reaction mixture.

24. A process of claim 23 wherein about 1.02 to about 1.06 moles of hydrogen peroxide per mole of tertiary amine are employed in forming the reaction mixture of step a).

25. A process of claim 11 wherein said tertiary amine is dodecyldimethyl amine or tetradecyldimethyl amine, wherein step a) is conducted in a reactor having suitably inert interior surfaces, wherein said shipping containers comprise a plurality of shipping containers having suitably inert interior surfaces, wherein the oxidation of step a) is conducted at one or more temperatures in the range of about 50 to about 55° C. during substantially all of step a), wherein a chelating agent is included in the reaction mixture of step a) in an amount in the range of about 0.01 to about 0.1 wt % based on the total weight of the reaction mixture, wherein about 1 to about 1.1 moles of hydrogen peroxide per mole of tertiary amine are employed in forming the reaction mixture of step a) and wherein the amount of water in the individual portions of the reaction mass dispensed into the containers in step b) is sufficient to form an aqueous solution containing approximately 30 wt % of the tertiary amine oxide.

* * * * *